US007807830B2

(12) United States Patent
Jobdevairakkam et al.

(10) Patent No.: US 7,807,830 B2
(45) Date of Patent: Oct. 5, 2010

(54) MANUFACTURE OF PURE HYDRALAZINE SALTS

(75) Inventors: Christopher N. Jobdevairakkam, Plainsboro, NJ (US); Jayaraman Kannappan, Gujrat (IN); Jagadeesh B. Rangisetty, Hyderabad (IN)

(73) Assignee: Navinta LLC, Ewing, NJ (US)

( * ) Notice: Subject to any disclaimer, the term of this patent is extended or adjusted under 35 U.S.C. 154(b) by 0 days.

(21) Appl. No.: 12/418,354

(22) Filed: Apr. 3, 2009

(65) Prior Publication Data

US 2009/0187018 A1 Jul. 23, 2009

Related U.S. Application Data

(62) Division of application No. 11/296,178, filed on Dec. 7, 2005, now Pat. No. 7,531,653.

(51) Int. Cl.
C07D 237/30 (2006.01)
(52) U.S. Cl. .................................................. 544/237
(58) Field of Classification Search .................. 544/237
See application file for complete search history.

(56) References Cited

U.S. PATENT DOCUMENTS

| 2,484,029 | A | 10/1949 | Hartmann et al. |
| 4,868,179 | A | 9/1989 | Cohn |
| 6,465,463 | B1 | 10/2002 | Cohn et al. |
| 6,784,177 | B2 | 8/2004 | Cohn et al. |
| 2003/0212272 | A1 | 11/2003 | Barbeau |
| 2005/0137198 | A1* | 6/2005 | Nelson et al. ............ 514/248 |
| 2005/0137397 | A1 | 6/2005 | Nelson |

FOREIGN PATENT DOCUMENTS

GB 629177 A 9/1949

OTHER PUBLICATIONS

Oates; "Antihypertensive Agents and Drug Therapy of Hypertension"; Goodman & Gilman's The Pharmacological Basis of Therapeutics (9th ed.), pp. 780-808, H; (New York: McGraw/Hill); 1996.

McFadden, et al.; "Cor pulmonale"; Heart Diseases. A Textbook of Cardiovascular-Medicine; 4th ed.; Philadelphia: WB Saunders, 1992; pp. 1581-1601.

Isaac; "Hydralazine and Psoriasis" British Medical Journal; 285:744; Sep. 11, 1982; 2 pages (abstract only).

Franciosa et al; "Hydralazine in the long-term Treatment of Chronic Heart Failure: Lack of Difference from Placebo"; Am. Heart .1, vol. 104, pp. 587-594 (1982).

Lessen, et al.; "Interactions Between Drug Substances and Excipients. 1. Fluorescence and HPLC Studies of Triazolophthalazine Derivatives from Hydralazine Hydrochloride and Starch"; J. Pharmaceutical Sci., 85(3): 326-329 (1996).

Chatterjee, et al.; "Oral Hydralazine in Chronic Heart Failure: Sustained Beneficial Hemodynamic Effects"; Annals of Internal Medicine; vol. 92; 1980; pp. 600-604.

Sinha and Motten; "Oxidative Metabolism of Hydralazine. Evidence for Nitrogen Centered Radicals Formation"; Biochemical and Biophysical Research Communications 105 (3); 1044-1051 (1982).

Gallagher, et al.; "Pharmacologic Approach to the Critically Ill Obstetric Patient," p. 847-862; The Pharmacologic Approach to the Critically Ill Patient; 3rd ed., Chernow, B (ed.) (Oates, IA: Williams & Wilkins, 1995).

Artman, et al.; "Short-term hemodynamic effects of hydralazine in infants with complete arterioventricular canal defects"; Circulation, 69; pp. 949-954 (1984).

Binkley, et al.; "Usefulness of hydralazine to withdraw from dobutamine in severe congestive heart failure"; Am. Cardia, 68:1103-1106 (1991).

* cited by examiner

*Primary Examiner*—Jafar Parsa
(74) *Attorney, Agent, or Firm*—St. Onge Steward Johnston & Reens LLC

(57) ABSTRACT

The present invention provides an improved process of preparing hydralazine hydrochloride, which involves the preparation of 1-chlorophthalazine salt and further reacting with hydrazine followed by purification of hydralazine hydrochloride, which is free of phosphate, does not contain any individual impurities more than 0.05%, total impurities less than 0.5%, and a hydrazine content of not more than 0.001%, and preferably less than 0.0003%. One benefit of improved purity is enhanced storage stability.

15 Claims, No Drawings

MANUFACTURE OF PURE HYDRALAZINE SALTS

CROSS-REFERENCE TO RELATED APPLICATIONS

This application is a divisional of U.S. patent application Ser. No. 11/296,178 filed on Dec. 7, 2005, the content of which is incorporated herein by reference.

FIELD OF THE INVENTION

This invention relates to methods for making hydralazine and its purification, including methods for making and purifying intermediates in the process.

BACKGROUND OF THE INVENTION

Hydralazine (e.g., Apresoline brand) is used to treat arterial hypertension (primary; malignant; pulmonary; pre-eclampsia and eclampsia), congestive heart failure, pulmonary hypertension in chronic obstructive pulmonary disease, and aortic regurgitation (McFadden, E R Jr & Braunwald, E., "Cor pulmonale," p. 1581-1601, *Heart Diseases. A Textbook of Cardiovascular-Medicine* (4th ed.) (Philadelphia: W B Saunders, 1992); Gallagher, M W; Repke, J T & Goldstein, P J (1994), "Pharmacologic Approach to the Critically Ill Obstetric Patient," p: 847-862, *The Pharmacologic Approach to the Critically Ill Patient* (3rd ed.), Chernow, B (ed.) (Oates, I A: Williams & Wilkins, 1995); *Antihypertensive Agents and Drug Therapy of Hypertension, Goodman & Gilman's The Pharmacological Basis of Therapeutics* (9th ed.), p. 809-838, Hardman, Limbird; Molinoff, Ruddon, and Gilman (eds.), (New York: McGraw/Hill); Chatterjee et al., *Ann. Intern. Merl*, Vol. 92, pp. 600-604 (1980); and Franciosa et al, *Am. Heart*.1, Vol. 104, pp. 587594 (1982). Some benefit may be seen if used in primary esophageal motility disorders (Mellow, M H, "Effect of isosorbide and hydralazine in painful primary esophageal motility disorders", *Gastroenterology*, 83:364-370 (1982)) and psoriasis (Isaac, P., "Hydralazine and psoriasis," *Br. Med. J.*, 285:744 (1982)). Recent observations indicate hydralazine can be used to withdraw patients from dobutamine in severe congestive heart failure (Binkley P F., et al., "Usefulness of hydralazine to withdraw from dobutamine in severe congestive heart failure," *Am. Cardia*, 68:1103-1106 (1991)). Infants with chronic heart failure and left-to-right shunts may experience some benefit with hydralazine use (Artman, M, et al., "Short-term hemodynamic effects of hydralazine in infants with complete arterioventricular canal defects," *Circulation*, 69:949-954 (1984)).

Uses of hydralazine along with other drugs have been reported by Jay Cohn et al. (U.S. Pat. Nos. 4,868,179, 6,784,177, and 6,465,463) for treating and preventing mortality associated with heart failure, improving oxygen consumption, quality of life and/or exercise tolerance in a black patient with hypertension.

Hydralazine hydrochloride is an artery specific direct peripheral vasodilator drug used to treat essential hypertension and it is commercially available in both oral and injectable dosage forms in the U.S. and other countries. Hydralazine hydrochloride is a drug having an onset of action with oral administration between 10-30 minutes (10-20 minutes given intravenously), a maximum hypotensive effect in 10-80 minutes, and duration of action between 3-4 hours.

Despite approval by the U.S. Food and Drug Administration (FDA) for administration of 20 mg hydralazine hydrochloride injectable doses, several clinical hazards are reported with the currently available hydralazine injectable formulations. Stability of the sterile injection solution is a serious problem due to the formation of particles in the hydralazine sterile injection solutions during storage for more than six months. These stability issues with hydralazine hydrochloride injectable solutions are likely due to the minor impurities present in the drug.

Donald has described in U.S. Patent Pub. 2003/0212272 that an injectable formulation of hydralazine forms small yellow-green particles following storage for one to two months at 40° C., and similarly after storage for six to nine months at 25° C. Although the identification of the yellow-green particles has yet to be confirmed, it is believed that the particles are insoluble polymeric products formed during storage of hydralazine—that the compound undergoes degradation in stored sterile injectable solutions, forming insoluble polymeric products because of the highly reactive hydrazino group. Hydralazine hydrochloride also undergoes several pharmaceutically undesirable reactions such as chelation with metal ions, oxidation, and pH-dependent decomposition. It is believed that these reactions, which often cause discoloration of hydralazine compositions, are also due to the highly reactive hydrazino group. Lessen et al., *J. Pharmaceutical Sci.*, 85(3): 326-329(1996), report that, in addition to the usual hydralazine degradants such as phthalazone and phthalazine, tablet compositions produced triazolophthalazine derivatives. Sinha and Motten, in *Biochemical and Biophysical Research Communications* 105(3). 1044-1051 (1982), report that hydralazine oxidizes rapidly in the presence of oxygen and metal compounds such as $Cu^{+2}$, $Fe^{+2}$, and $Fe^{+3}$ through free radical intermediates, much like other hydrazine derivatives.

As described in the art, the hydralazine drug molecule is sensitive to excipients reactive with its hydrazine moiety. In addition to excipients, impurities present in the drug substance play a key role in causing instability of sensitive molecules such as hydralazine. Thermal degradation and hydrolysis of hydralazine gives phthalazinone, phthalazine, and triazolophthalazine. Producing hydralazine hydrochloride in significantly purer form would significantly improve the stability of the product and thus maintain its safety and efficacy.

The first process of preparing hydralazine (1-hydrazinophthalazine) and its salts was reported in U.S. Pat. No. 2,484,029 and British Pat. No. 629,177. This process involved the preparation of 1-chlorophthalazine (from phthalazinone by the process reported in *Ber. D. deutsch. chem. Ges.*, Vol., 26, page 521 (1893)), and the freshly obtained yet moist chloro compound was further reacted with a mixture of 100 parts by volume of ethyl alcohol and 90 parts by volume of hydrazine hydrate. The hydralazine thus obtained was recrystallized from methanol and converted to the hydrochloride salt on warming in alcoholic or aqueous hydrochloric acid. Hydralazine hydrochloride obtained by this process is found to contain several impurities at about 0.5%, has a greater than 0.01% level of hydrazine content, and does not comply with the present pharmacopoeial requirements for the drug. The U.S. Pharmacopoeia requires the hydralazine drug substance to be free of hydrazine at a level less than 0.001%, and the European Pharmacopoeia requires any individual impurities to be present at levels not more than 0.2%.

More recently, U.S. Patent Pub. 2005/0137397 (the '397 application) discloses the process of preparing hydralazine hydrochloride involving the preparation of chlorophthalazine from phthalazinone and phosphorous oxychloride, separating using a first solvent such as an alkane having 5 to 7 carbons and a second solvent (such as tetrahydrofuran), reacting the isolated chlorophthalazine with hydrazine in presence of alcohol to produce hydralazine, and treating the hydralazine with hydrochloric acid to yield hydralazine hydrochloride. It is disclosed that the product hydralazine hydrochloride obtained by this process contains phthalazine impurities less than 0.5% and hydrazine content less than 0.0005%.

The process of the '397 application has a number of drawbacks. The chlorophthalazine prepared as disclosed in this publication was found to contain more insoluble matter. In addition, the process of isolating chlorophthalazine, as disclosed in this publication, involves decanting a supernatant liquid mixture containing several volumes of hexane and phosphorous oxychloride, a cumbersome operation and that is a serious limitation towards scaling-up the disclosed process. The description in the '397 application of the hydralazine hydrochloride produced is pale yellow in color, and off-white after recrystallization from ethanol.

There is no reported procedure in the art for the purification of hydralazine to remove the yellow color and for the reduction of hydrazine content to a level of below 0.001%.

Hydralazine hydrochloride is one of the drugs known for its instability in injectable solution during storage. This problem calls for the need of a process to produce hydralazine hydrochloride free of significant level of impurities and for the need of a process of purification of impure hydralazine hydrochloride

SUMMARY OF THE INVENTION

It is a prime object of this invention to provide a commercially viable manufacturing process for preparing hydralazine hydrochloride in significantly purer form containing any individual impurity not more than 0.05%, total impurities less than 0.5%, and a hydrazine content not more than (NMT) 0.001%.

The present invention describes a novel process of producing pure hydralazine useful for, among other conditions, the treatment of hypertension and related heart diseases.

The present invention provides a number of novel improvements that provide a safer and simpler routes or subprocesses to intermediates useful in the production of hydralazine, and ultimately allow production of pure hydralazine salts, with fewer impurities.

Another important aspect of this invention is to provide a novel process for purifying hydralazine hydrochloride by using an aqueous medium to remove the yellow coloration and to reduce hydrazine content to a level below 0.001%.

Yet another novel aspect of the process of this invention is the isolation of chlorophthalazine as a mineral acid salt or salt mixture, without distillation or the need to concentrate the reaction mass. This novel process of isolation is commercially viable and can be scaled up to production level. In addition, the amount of phosphorous oxychloride used is less than 1 mol equivalent to phthalazinone, providing low exothermicity and therefore a safer process, especially when scaled-up; the prior art has always suggested use of phosphorous oxychloride at much higher level of about 4 mol equivalent. The additional purification process of treating hydralazine solution with activated carbon and chelating agents allows removal of yellow color of the material.

In summary, one embodiment of this invention provides a novel improved process of: a) reacting phthalazinone with about one mole equivalent of phosphorus oxychloride and then acidifying the medium to produce a 1-chlorophthalazine salt optionally in admixture with a mineral acid; b) reacting the product of step (a) with hydrazine in an aqueous or alcoholic, and otherwise essentially non-organic, medium to produce hydralazine base; and c) converting the hydralazine base to hydralazine hydrochloride. Further, the present invention provides a novel improved process of purification of the hydralazine hydrochloride, which can be performed by dissolution in aqueous medium followed by treatment with an adsorbent and/or chelating agent, removal of the same, and precipitation of the final product by cooling.

DETAILED DESCRIPTION OF THE INVENTION

This invention relates to a number of novel process steps and combinations thereof in the preparation of hydralazine, including obtaining pure chlorophthalazine salt by a precipitation process, forming hydralazine base in the absence of an organic solvent, and a novel process of purifying hydralazine hydrochloride.

The process according to one embodiment of this invention comprises the steps of: a) reacting phthalazinone with an approximately equimolar equivalent of phosphorous oxychloride at a specific temperature to produce a 1-chlorophthalazine salt; b) isolating the 1-chlorophthalazine salt formed in step (a) by precipitating the 1-chlorophthalazine salt by adding a mineral acid in the presence of solvent and filtering and drying the solid 1-chlorophthalazine salt; c) reacting the isolated and dried 1-chlorophthalazine salt with hydrazine hydrate without any organic solvent and precipitating the hydralazine base by adding a solvent; d) purifying the hydralazine base in a non-aqueous medium; e) converting the purified hydralazine base to hydralazine hydrochloride in a non-aqueous medium and isolating therein; and f) purifying the isolated hydralazine hydrochloride in aqueous medium According to another embodiment, this invention provides a process for purifying hydralazine hydrochloride comprising the steps of: a) dissolving hydralazine hydrochloride in hot water; b) treating the solution with color adsorbent and a chelating agent; c) filtering off the adsorbent and chelating agent; d) adjusting the pH of the mixture; and e) precipitating hydralazine hydrochloride by adding a water miscible solvent at a lower temperature.

In one preferred embodiment of the process of this invention, phthalazinone was reacted with phosphorous oxychloride in toluene at a temperature of about 45° C. to about 65° C. for about 3 hours. Ethyl acetate and sulfuric acid were added to complete the precipitation of the 1-chlorophthalazine salt. The product 1-chlorophthalazinone hydrochloride/sulfate salt produced as such was significantly free of chlorophosphorylphthalazine.

In another preferred embodiment of this invention, pure hydralazine base was prepared by the reaction of 1-chlorophthalazinehydrochloride/sulfate salt with an excess of hydrazine hydrate at a predetermined temperature (preferably between 0° and about 30° C.) without the presence of an organic solvent during the reaction. After completion of the reaction (which can be monitored by HPLC analysis), the hydralazine base was precipitated by adding methanol to the reaction mixture. Alternatively, the reaction can be conducted in the presence of a short-chain aliphatic alcohol, preferably having one to four carbon atoms, but is otherwise essentially free from organic solvents. As used in connection with the medium in which hydrazine is used to produce hydralazine, "consisting essentially of a non-organic medium" and terms to that effect are intended to include aliphatic alcohols and to exclude aryl compounds and longer chain alcohols.

The hydralazine base obtained by the process of this invention was pale yellow in color. It was purified by using activated carbon treatment in methanol and then purified and recovered while in methanol by purging the solution with hydrochloric acid gas to precipitate hydralazine hydrochloride. The hydralazine hydrochloride isolated by filtration was further purified by dissolving the crude hydrochloride in hot water in the presence of activated carbon and a chelating agent such as EDTA. The carbon and EDTA suspension were then filtered off from the hot solution, adjusting the pH of the mixture using an acid or base and the pure hydralazine hydrochloride was obtained by cooling the pH adjusted mixture followed by precipitating by the addition of methanol.

In another major embodiment of this invention, a process of preparing pure hydralazine hydrochloride is disclosed, comprising the steps of: a) reacting phthalazinone with phosphorous oxychloride at a specific temperature to produce 1-chlorophthalazine salt; b) concentrating the reaction mixture by distillation; c) isolating the 1-chlorophthalazine salt concentrated in step (b) by precipitating 1-chlorophthalazine salt through the addition of a mineral add in the presence of a solvent, filtering the resulting solid precipitated 1-chtorophthalazine salt, and drying; d) reacting the isolated and dried 1-chlorophthalazine salt with hydrazine hydrate without any substantial amount of organic solvent present and precipitating the resulting hydralazine base by adding a solvent; e) purifying the hydralazine base in a non-aqueous medium; f) converting the purified hydralazine base to hydralazine hydrochloride in a non-aqueous medium, and isolating the same; and g) purifying the isolated hydralazine hydrochloride by dissolving hydralazine hydrochloride in hot water to make a solution, treating the solution with a color adsorbent and a chelating agent, filtering off the adsorbent and chelating agent, adjusting the pH of the solution using a base or acid, and precipitating hydralazine hydrochloride by adding a water miscible solvent at a lower temperature.

In one preferred embodiment of the process of this invention, phthalazinone was reacted with phosphorous oxychloride at a temperature of about 45° C. to about 65° C. for about 3 hours. The reaction mass was concentrated by distilling out about 65% of the phosphorous oxychloride under vacuum (about 600 to 700 mm of mercury) and at an elevated temperature (about 45° to about 55 ° C.). To the concentrated reaction mass a predetermined quantity of concentrated sulfuric acid was added at a controlled temperature followed by the addition of ethyl acetate to precipitate the 1-chlorohydrochloride/sulfate mixture. The product 1-chlorophthalazinone hydrochloride/sulfate salt produced as such was significantly free of chlorophosphorylphthalazine.

It is preferred that phthalazinone and phosphorous oxychloride are present in an approximately molar ratio of less than 1:4, respectively, more preferably not more than about 1:3, more preferably not more than about 1:2, and most preferably about 1:1. A reduction in the presence of the phosphorous oxychloride means the reaction is less exothermic and thus safer, and more amenable to scaling-up.

The mineral acid used to isolate a 1-chlorophthalazine can be any mineral acid suitable for forming a desired salt, such as a chloride or sulfate; hydrochloric and sulfuric acids, and mixtures thereof, are preferred.

In the preparation of 1-chlorophthalazine, the solvent used is an organic solvent, such as toluene, ethyl acetate, or tetrahydrofuran; any suitable solvent can be used. Preferred are non-polar and slightly polar solvents like methyl acetate and ethyl acetate, and similar solvents. On the other hand, in the reaction with hydrazine hydrate, in which the medium contains essentially no organic solvent, the product is recovered using an organic solvent, preferably an aliphatic alcohol (such as methanol, ethanol, isopropanol, or a combination thereof). In the conversion from hydralazine base to hydralazine hydrochloride, the organic solvent can be an aliphatic alcohol, tetrahydrofuran, and the like. In the purification process in which the pH is adjusted, prior to precipitation, the pH adjustment is preferably done by using a base. The base is preferably a mono-, di-, or trialkylamine, arylamine, or aralkyl amine, or a sodium base, or a compatible mixture thereof. Examples of suitable bases include diethylamine, triethylamine, sodium hydroxide, sodium bicarbonate, sodium carbonate, diisopropylethylamine, isopropyldiethylamine, and the like.

In the purification process using a chelating agent, preferred chelating agents are organic and include those with at least one carboxyl group, such as ethylenediaminetetraacetic acid (EDTA), ethylene glycol-his-(13-amino-ethylether)-N, N,N',N'-tetraacetic acid (EGTA), and cyclohexane-1,2-diaminetetraacetic acid (CDTA).

Further details of this invention are shown in the following examples, which should be taken as descriptive and illustrative of aspects of the invention and not limiting the scope of the invention.

EXAMPLE 1 (COMPARATIVE)

Preparation of 1-chlorophthalazine

According to the process disclosed in U.S. Patent Pub. 20050137397, the disclosure of which is incorporated herein by reference, one mole equivalent (250 g) of 1 (2H)-phthalazinone and 3.8 mole equivalents (775 g) of phosphorus oxychloride were charged into a 3-L, 3-necked flask fitted with a temperature probe and condenser. The slurry was stirred and heated to 80° C., maintained at that temperature for 30 minutes, and then the heat source was removed. The mixture was allowed to cool to room temperature and 1.6 L of hexane were added. The resulting slurry was stirred for about 30 minutes, allowed to settle, and the hexane layer was decanted; the addition of hexane and decantation was repeated three times. Then 1.6 L of tetrahydrofuran was added to the slurry and a yellow precipitate formed. The yellow solid (reported in the '397 application as an off white solid) was isolated by filtration and then washed with 250 mL of cold tetrahydrofuran to afford a 50% yield (reported yield in the '397 application is 85 to 100%) of 1-chlorophthalazine.

EXAMPLE 2 (COMPARATIVE)

Preparation of Hydralazine

Again according to the disclosure in the '397 application, to a 2-L, 3-necked, round-bottomed flask fitted with a temperature probe and condenser were charged 700 mL of ethanol and 7.6 mole equivalents (630 mL) of hydrazine hydrate, and the solution was cooled to 50° C. (the '397 application discloses a temperature <10° C.). One (1) mole equivalent (280 g) of 1-chlorophthalazine (solid) was added in portions at a rate to maintain the solution temperature at <20° C. The solution was stirred and heated to 60-70° C. After one hour at that elevated temperature, the hot solution was filtered to remove any insoluble by-products (insoluble matter recovered was 12 g), and the filtrate was cooled to 0 to 5° C. A light yellow solid formed in the cold solution, which was isolated by filtration, washed with cold ethanol, and then dried to constant mass and characterized. The yield was 80% (the yield reported in the '397 application was 77-80%).

EXAMPLE 3 (COMPARATIVE)

Preparation of Hydralazine Hydrochloride

Again according to the disclosure in the '397 application, hydralazine free base 25 g (1 part by weight) was heated in 165 mL (6 to 7 parts by volume) of 15% hydrochloric acid to a temperature of 70-80° C. The solution was filtered hot to remove traces of insoluble materials that were undesired byproducts of the preceding step. One hundred sixty five milliliters of ethanol (6 to 7 parts by volume) was added to the filtrate. As the resulting solution cooled to 25° C. (ambient temperature) and then further cooled to 3-8° C., a pale yellow precipitate of the desired product, hydralazine hydrochloride, solidified. The obtained yield is 65% (the reported yields in the '397 application were 80-90%).

EXAMPLE 4 (COMPARATIVE)

Recrystallization of Hydralazine Hydrochloride

Again according to the '397 application, a single necked, round-bottomed flask was charged with 10 g (1 part by weight of hydralazine hydrochloride) (from Example 3) and 60 mL (6 parts by volume) of 1% hydrochloric acid. The solution was stirred and heated to dissolve the solid, and then filtered hot, if necessary, to remove traces of colored insoluble byproducts. Sixty milliliters of ethanol (6 parts by volume) was added to the hot (filtered) solution. As the resulting solution cooled, a pale yellow precipitate (reported in the '397 application as an off-white precipitate) of purified hydralazine hydrochloride formed. The recrystallized, product was isolated by filtration and washed with fresh, cold ethanol. The isolated material was analyzed for impurities and hydrazine content with the following results: hydrazine content=0.0004%; yield 90% (reported yield in the '397 application is 85 to 100%).

EXAMPLE 5A

Preparation of 1-chlorophthalazine Hydrochloride and Sulfate Mixture

A 3-neck 2 L round-bottomed flask was charged with 584 mL of phosphorous oxychloride (306 g, 2 mol. eq.) and cooled to about 0 to 5° C. To this was added 73 g (0.5 mol eq.) of powdered phthalazinone (1-2H-phthalazinone). The reaction mass appeared as a suspension and was stirred at about 60° C. for about 1 hour. The progress of the reaction was monitored by HPLC. The reaction mixture was maintained at about 50° C. and about 65% of the phosphorous oxychloride was distilled out under vacuum at that thereby concentrating the solution. The resulting concentrated reaction mixture was cooled to room temperature and about 375 mL of ethyl acetate were added with stirring and cooling to about 0 to 5° C. The resulting pale yellow material was filtered and washed with 150 mL of ethyl acetate, and the washing was combined with the mother liquor. To the mother liquor was added 12 mL of concentrated sulfuric acid with stirring at 0 to 5° C. for about one hour. The resulting precipitated 1-chlorophthalazine sulfate was filtered and washed with cold ethyl acetate. The isolated 1-chlorophthalazine salts combined and dried under vacuum for about 3 hours at 30° C. Yield=65%; purity=99%.

EXAMPLE 5B

Preparation of 1-chlorophthalazine Hydrochloride and Sulfate Mixture

A 3-neck 2 L round-bottomed flask was charged with phosphorous oxychloride (306g, 2 mol. eq.) and cooled to about 0 to 5° C. To this added 73 g of powdered phthalazinone (0.5 mol eq.) The reaction mass appear as a suspension and was stirred at about 60° C. for about 3 hours. The progress of the reaction was monitored by HPLC. While the reaction mixture was maintained at 50°-60° C., about 65% of the phosphorous oxychloride was distilled out under vacuum. The concentrated reaction mixture was cooled to room temperature and about 375 mL of Ethyl acetate and 12 mL of concentrated sulfuric acid were added, the mixture then stirred for about 1 hour while cooled to 0 to 5° C. The resulting pale yellow material was filtered and washed with 150 mL of cold ethyl acetate. The isolated material was 1-chlorophthalazine salt mixture, which was then dried under vacuum for about 3 hours at 30° C. Yield=65%; purity=99%.

EXAMPLE 5C

Preparation of 1-chlorophthalazine Hydrochloride and Sulfate Mixture

A 3-neck 2 L round-bottomed flask was charged with 300 mL toluene and 146 g (1 mol eq.) of phthalazinone. Added slowly dropwise to the flask was 146 mL of phosphorous oxychloride (1.5 mol. eq.) at room temperature. The temperature shot up to about 45° C. The reaction mass was heated to about 60° C. and maintained at a temperature between 60 to 65° C. for about 3 hours. The progress of the reaction was monitored by HPLC. After completion, the reaction mixture was cooled to about 5° C. and the precipitation of 1-chlorophthalazine appears. Thereafter were added about 800 mL ethylacetate and 24 mL of concentrated sulfuric acid with stirring for about an hour. The precipitated 1-chlorophthalazine salt was filtered, washed with acetone and dried under vacuum for about 5 hours at 45° C. Yield=85%; purity=99%.

EXAMPLE 5D

Preparation of 1-chlorophthalazine Hydrochloride and Sulfate Mixture

A 3-neck 2 L round-bottomed flask was charged with 300 mL toluene and 146 g (1 mol eq.) of phthalazinone. Slowly added dropwise was 292 mL of phosphorous oxychloride (3.0 mol. eq.) at room temperature. The temperature shot up to about 45° C. The reaction mass was heated to about 60° C. and maintained at a temperature between 60 to 65° C. for about 3 hours. The progress of the reaction was monitored by HPLC. The reaction mixture was cooled to about 5° C., after which about 800 mL of ethylacetate and 24 mL of concentrated sulfuric acid was added with stirring for about an hour. The precipitated 1-chlorophthalazine salt was filtered, washed with acetone and dried under vacuum for about 5 hours at 45° C. Yield=70%; purity=99%; the ratio of 1-chlorophthalazine hydrogen sulfate to 1-chlorophthalazine hydrochloride was about 3:2 by weight.

EXAMPLE 6

Preparation of 1-chlorophthalazine Hydrochloride

A 3-neck 2 L round-bottomed flask was charged with phosphorous oxychloride (306 g, 2 mol. eq.) and cooled to about 0 to 5° C. To this was added 73 g of powdered phthalazinone (0.5 mol eq.). The reaction mass appeared as a suspension and was heated to about 60° C. with stirring. The progress of the reaction was monitored by HPLC. While the reaction mixture was maintained at approximately 50° C., about 65% of the phosphorous oxychloride was distilled out under vacuum. The concentrated reaction mixture was cooled to room temperature, about 375 mL of ethyl acetate was added, and then the mixture was purged with HCl gas for about 30 min; thereafter, the mixture was cooled to a temperature of 0 to 5° C. and stirred for about one hour. The resulting pale yellow material was filtered and washed with 150 mL of cold ethyl acetate. The isolated material was 1-chlorophthalazine hydrochloride, which was dried under vacuum for about 3 hours at 30° C. Yield=65%; purity=99%.

EXAMPLE 7A

Preparation of Hydralazine Base in the Absence of Organic Solvent

A 2 L, 3-necked, round-bottomed flask fitted with a temperature probe and condenser, and was charged 375 mL of hydrazine hydrate; the solution was then cooled to 0 to 5° C. About 75 g of 1-chlorophthalazine salt was added in portions at a rate to maintain the solution temperature at 0 to 5° C. After addition, the solution was stirred at 20 to 25° C. for about 24 hours. The reaction mixture was then cooled to 0 to 5° C. and 150 mL of methanol was added, the solution stirred for 3 hours, and the resulting solid material was filtered, washed with 150 mL of cold methanol, and dried under vacuum at 35° C. Yield=99%.

EXAMPLE 7B

Preparation of Hydralazine Base Using Isopropanol

A 500 mL, 3-necked, round-bottom flask fitted with a temperature probe and condenser was charged with 45 mL of hydrazine hydrate and 25 mL of isopropanol; the solution was cooled to 0 to 5° C. About 9 g of 1-chlorophthalazine salt were added in portions at a rate to maintain the solution temperature at 0 to 5 degrees. The solution was stirred at 20 to 25° C. for about 24 hours. The reaction mixture was then cooled to 0 to 5° C. and stirred for 3 hours. The resulting solid material was filtered from the solution, washed with 15 mL of cold isopropanol, and dried under vacuum at 35° C. Yield=86%.

EXAMPLE 7C

Preparation of Hydralazine Base Using Ethanol

A 500 mL, 3-necked, round-bottom flask fitted with a temperature probe and condenser was charged with 45 mL of hydrazine hydrate; 25 mL of ethanol, and the solution was cooled to 0 to 5° C. About 9 g of 1-chlorophthalazine salt was added in portions at a rate to maintain the solution temperature at 0 to 5 degrees. The solution was stirred at 20 to 25° C. for about 24 hours. The reaction mixture was then cooled to 0 to 5° C. and stirred for 3 hours. The solid material obtained was filtered, washed with 15 mL of cold ethanol, and dried under vacuum at 35° C. Yield=90%.

EXAMPLE 8

Preparation of Hydralazine Hydrochloride

Hydralazine free base 45 g (prepared by the process of example 7A) was dissolved in 1125 mL of methanol, 5 g activated carbon was added, and the mixture stirred for about 30 minutes. The carbon was removed by filtration and the clear filtrate was collected and then purged with HCl gas for about 15 minutes. The resultant reaction mass is cooled to 0 to 5° C., the precipitated off-white hydralazine hydrochloride was filtered, and then washed with cold methanol.

EXAMPLE 9A

Purification of Hydralazine Hydrochloride

Hydralazine hydrochloride wet material obtained by the process of Example 8 was suspended in 400 mL methanol. Then 40 mL of triethylamine was added and the temperature was raised to about 60 to 65° C. to get a clear solution; the hot solution was filtered to remove insoluble matter, if any. Hydrogen chloride gas was purged through the solution/filtrate to reach a pH of 2 to 4. The slurry mass was cooled to about 0 to 5° C., stirred for about 1 hour, filtered, washed with 80 mL of cold methanol to isolate purified hydralazine hydrochloride, and dried under vacuum at 45° C. for about 3 hours. The dried material was suspended in 370 mL of water and the temperature was raised to about 75 to 80° C. to get a clear solution. About 3.7 g of activated carbon and 0.5 g of EDTA were added, and the solution stirred for about 30 minutes at 75 to 80° C. The carbon was filtered from the hot solution, about 450 mL of methanol was added, and the solution was cooled to 0 to 5° C. The cold mixture was further cooled to about −20° C. From the resulting solid, pure hydralazine hydrochloride was obtained by filtering, washing with cold methanol, and drying under vacuum. A white precipitate of hydralazine hydrochloride obtained was analyzed by HPLC for impurities and hydrazine content with following results: hydrazine content=0.00004%; yield about 95%.

EXAMPLE 9B

Purification of Hydralazine Hydrochloride

Hydralazine hydrochloride wet material obtained by the process of Example 8 was suspended in 370 mL of water and the temperature was raised to about 75 to 80° C. to get a clear solution. About 17 g of activated carbon and 0.5 g of EDTA were added, and the solution stirred for about 30 minutes at 75° to 80° C. The carbon was filtered from the hot solution, about 450 mL of methanol was added, the solution cooled to room temperature. The pH of the solution was adjusted with dilute sodium hydroxide solution to about 3 to 4.5 and the solution was then cooled to 0° to 5° C. The cold mixture was further cooled to about −20° C. From the resulting solid, pure hydralazine hydrochloride was obtained by filtering, washing with cold methanol, and finally drying under vacuum. The dried white precipitate of hydralazine hydrochloride obtained was analyzed by RPLC for impurities and hydrazine content: hydrazine content=0.00004%; yield about 95%.

EXAMPLE 9C

Purification of Hydralazine Hydrochloride

Hydralazine hydrochloride wet material obtained by the process of Example 8 was suspended in 370 mL of water and the temperature was raised to about 75 to 80° C. to get a clear solution. About 3.7 g of activated carbon and 0.5 g of EDTA were added, and the solution stirred for about 30 minutes at 75 to 80° C. The carbon was filtered from the hot solution, about 450 mL of methanol was added, and the solution cooled to room temperature. pH of the solution was adjusted with sodium bicarbonate to about 3 to 4.5 and the solution was cooled to 0 to 5° C. The cold mixture was further cooled to about −20° C. From the resulting solid, pure hydralazine hydrochloride was obtained by filtering, washing with cold methanol, and drying under vacuum. A white precipitate of hydralazine hydrochloride obtained was analyzed by 1-1 PLC for impurities and hydrazine content: hydrazine content=0.00004%; yield about 95%.

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A process of purifying hydralazine hydrochloride comprising the steps of:
    (a) performing a temperature-assisted dissolution of hydralazine hydrochloride in an aqueous solvent;
    (b) treating the solution with a clarifying agent selected from chelating agents, activated carbon, and mixtures thereof;
    (c) removing the clarifying agents by filtration and optionally adjusting the pH of the filtrate with acid or base to about 2 to 5; and
    (d) precipitating hydralazine hydrochloride from the filtrate by cooling, wherein the hydrazine content is reduced to a level of below 0.001%.

2. The process of claim 1, wherein the step of precipitating hydralazine hydrochloride occurs in water.

3. The process of claim 1, wherein the step of precipitating hydralazine hydrochloride occurs in an aqueous solvent mixture containing one or more water miscible organic solvents.

4. The process of claim 3, wherein the water miscible organic solvent is a lower alkyl alcohol, tetrahydrofuran, acetonitrile, or a mixture thereof.

5. The process of claim 4, wherein the alcohol is selected from the group consisting of methanol, ethanol, isopropanol, and mixtures thereof.

6. The process of claim 1, wherein the aqueous solvent in step (a) is water.

7. The process of claim 1, wherein the aqueous solvent in step (a) is an aqueous solvent mixture containing one or more water miscible organic solvents.

8. The process of claim 1, wherein the base is an amine, a hydroxide, a carbonate, a bicarbonate, or a mixture thereof.

9. The process of claim 8, wherein the amine is an alkyl amine selected from the group consisting of triethylamine, diethylamine, diisopropylamine, diisopropylethylamine, piperidine, alkylpiperidines and mixtures thereof.

10. The process of claim 8, wherein the amine is an alkyl aryl amine selected from the group consisting of N-alkylanilines, pyridines, and mixtures thereof.

11. The process of claim 8, wherein the hydroxide is sodium hydroxide, potassium hydroxide, lithium hydroxide, tetraalkylammonium hydroxide, or a mixture thereof.

12. The process of claim 8, wherein the bicarbonate or carbonate is a salt of sodium or potassium or a mixture thereof.

13. The process of claim 1, wherein the acid in step (c) is hydrochloric acid.

14. The process of claim 1, wherein the chelating agent contains at least one carboxyl functional group.

15. The process of claim 14, wherein the chelating agent is ethylenediamine tetraacetic acid (ETDA), ethylene glycol-bis-(beta-amino-ethylether) N,N,N',N'-tetraacetic acid (EGTA), cyclohexane-1,2-diaminetetraacetic acid (CDTA), or a mixture thereof.

* * * * *